United States Patent
Sahai et al.

(10) Patent No.: US 9,827,015 B1
(45) Date of Patent: Nov. 28, 2017

(54) WIRELESS PEDICLE SCREW SYSTEM AND METHODS OF USE

(71) Applicant: Spine Ortho Center, P.A., Deerfield Beach, FL (US)

(72) Inventors: Ashish K. Sahai, Deerfield Beach, FL (US); Nikhil Sahai, Deerfield Beach, FL (US)

(73) Assignee: SPINE ORTHO CENTER, P.A., Deerfield Beach, FL (US)

(*) Notice: Subject to any disclaimer, the term of this patent is extended or adjusted under 35 U.S.C. 154(b) by 0 days.

(21) Appl. No.: 14/480,438

(22) Filed: Sep. 8, 2014

Related U.S. Application Data

(60) Provisional application No. 61/874,411, filed on Sep. 6, 2013.

(51) Int. Cl.
  *A61M 29/00* (2006.01)
  *A61B 17/70* (2006.01)

(52) U.S. Cl.
  CPC .................. *A61B 17/7002* (2013.01)

(58) Field of Classification Search
  CPC ........................................ A61B 1/32
  USPC ......................................... 606/916
  See application file for complete search history.

(56) References Cited

U.S. PATENT DOCUMENTS

| | | | | |
|---|---|---|---|---|
| 3,892,232 A | * | 7/1975 | Neufeld | A61B 17/742 606/104 |
| 6,200,322 B1 | * | 3/2001 | Branch | A61B 17/1757 606/104 |
| 6,267,763 B1 | * | 7/2001 | Castro | A61B 17/025 606/100 |
| 6,610,059 B1 | * | 8/2003 | West, Jr. | A61B 17/32002 606/41 |
| 2003/0083688 A1 | * | 5/2003 | Simonson | A61B 17/0218 606/191 |
| 2009/0125030 A1 | * | 5/2009 | Tebbe | A61B 17/3421 606/90 |
| 2009/0306671 A1 | * | 12/2009 | McCormack | A61B 17/025 606/90 |
| 2014/0257489 A1 | * | 9/2014 | Warren | A61B 17/1671 623/17.16 |

* cited by examiner

*Primary Examiner* — Jan Christopher Merene
(74) *Attorney, Agent, or Firm* — McHale & Slavin, P.A.

(57) ABSTRACT

A wireless pedicle screw system and method of use for fixation and/or stabilization of vertebral bodies using pedicle screws and rods or plates is described. The wireless pedicle screw system includes a dilator tube having a generally elongated body defined by a continuous wall. The elongated body has a proximal end, a distal end, and an inner lumen running the length of the elongated body sized to receive and enclose various pedicle screw implant instruments. Positioned at the distal end are alignment/positioning members constructed to properly aid a surgeon in aligning the dilator tube to portions of the vertebra. Proper placement about the vertebra using the engagement members results in the ability to insert pedicle screws, resulting in minimizing tissue trauma, reducing operating room time, reducing X-Ray radiation exposure, and eliminating the need for k-wire guidance.

8 Claims, 7 Drawing Sheets

WIRELESS PEDICLE SCREW SYSTEM AND METHODS OF USE

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/874,411, entitled "WIRELESS PEDICLE SCREW SYSTEM AND METHODS OF USE", filed Sep. 6, 2013. The contents of the above referenced application is incorporated herein by reference in its entirety.

FIELD OF THE INVENTION

The present invention relates to instruments and methods for use with spinal surgeries. More specifically, the present invention relates to a wireless pedicle screw system and methods of use for fixation and/or stabilization of vertebral bodies using pedicle screws and rods or plates.

BACKGROUND OF THE INVENTION

A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints, allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the anulus fibrosus ("anulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae. The anulus of the disc forms the disc perimeter, and is a tough, outer fibrous ring that binds adjacent vertebrae together. The fibrous layers of the anulus include fifteen to twenty overlapping plies, which are inserted into the superior and inferior vertebral bodies at roughly a 40-degree angle in both directions. This causes bi-directional torsional resistance, as about half of the angulated fibers will tighten when the vertebrae rotate in either direction. It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the anulus to buckle in areas where the laminated plies are loosely bonded. As the overlapping laminated plies of the anulus begin to buckle and separate, either circumferential or radial anular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. In other cases it is desired to fuse the adjacent vertebrae together after removal of the disc, sometimes referred to as "intervertebral fusion" or "interbody fusion." In this process, spondylodesis or spondylosyndesis is used to join two or more vertebrae to eliminate pain caused by abnormal motion, degradation, fractures or deformities of the vertebrae.

SUMMARY OF THE INVENTION

The present invention relates to a wireless pedicle screw system and methods of use for fixation and/or stabilization of vertebral bodies using pedicle screws and rods or plates. The wireless pedicle screw system includes a dilator tube adapted to engage portions of vertebra. The dilator tube in accordance with the present invention includes a generally elongated body having a continuous wall to define a generally cylindrical shape. The elongated body has a proximal end, a distal end, and an inner lumen running the length of the elongated body, extending from the proximal end to the distal end. The inner lumen is sized to receive and enclose various pedicle screw implant instrumentation. Positioned at the distal end are a plurality of alignment or positioning members constructed to properly align the dilator to portions of the vertebra to aid in the insertion of pedicle screws into the pedicle in a manner which reduces tissue trauma, reduces Operating Room (OR) time, reduces X-Ray radiation exposure, and eliminates the need for k-wire guidance.

Accordingly, it is an objective of the present invention to provide a wireless pedicle screw system and methods of use for fixation and/or stabilization of vertebral bodies using pedicle screws and rods or plates.

It is a further objective of the present invention to provide a wireless pedicle screw system and methods of use for fixation and/or stabilization of vertebral bodies using pedicle screws and rods or plates which reduces tissue trauma.

It is yet another objective of the present invention to provide a wireless pedicle screw system and methods of use for fixation and/or stabilization of vertebral bodies using pedicle screws and rods or plates, which reduces Operating Room (OR) time.

It is a still further objective of the invention to provide a wireless pedicle screw system and methods of use for fixation and/or stabilization of vertebral bodies using pedicle screws and rods or plates which reduces the amount of X-Ray radiation exposure to the patient.

It is a further objective of the present invention to provide a wireless pedicle screw system and methods of use for fixation and/or stabilization of vertebral bodies using pedicle screws and rods or plates which eliminates the need for k-wire guidance.

It is yet another objective of the present invention to provide a wireless pedicle screw system and methods of use for fixation and/or stabilization of vertebral bodies using pedicle screws and rods or plates which includes a dilator tube adapted to contain a plurality of alignment members.

It is a still further objective of the invention to provide a wireless pedicle screw system and methods of use for fixation and/or stabilization of vertebral bodies using pedicle screws and rods or plates which includes a dilator tube having a transverse process side window.

It is a further objective of the present invention to provide a wireless pedicle screw system and methods of use for fixation and/or stabilization of vertebral bodies using pedicle screws and rods or plates which includes a dilator tube having a facet flat edge recess.

It is yet another objective of the present invention to provide a wireless pedicle screw system and methods of use for fixation and/or stabilization of vertebral bodies using pedicle screws and rods or plates which includes a dilator tube having a transverse process side window and a diametrically opposing facet flat edge recess.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
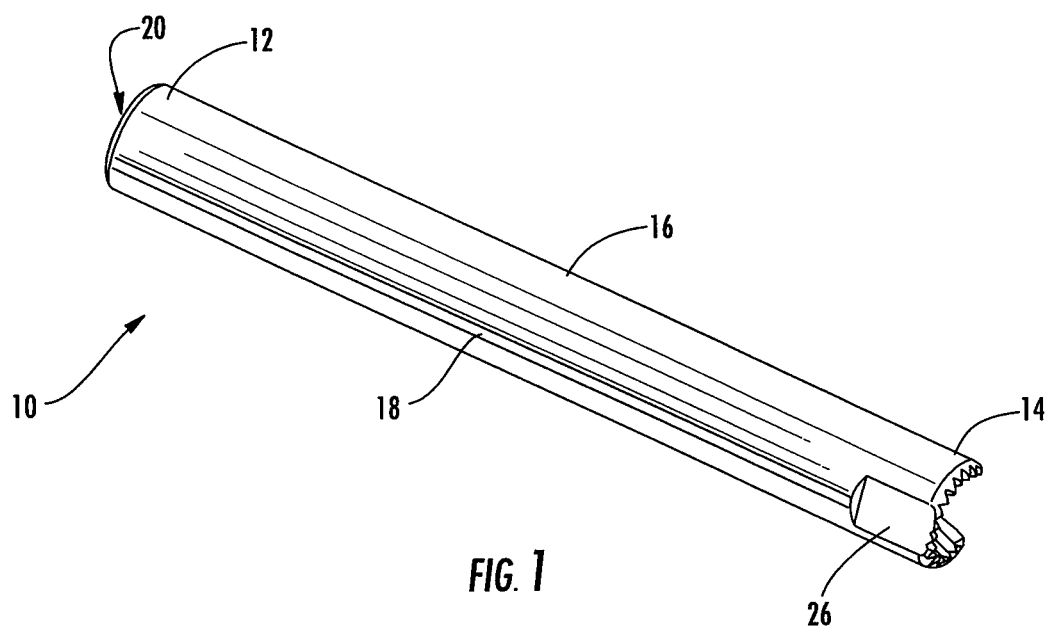
FIG. 1 is a perspective view of a dilator tube.
Figure 2:
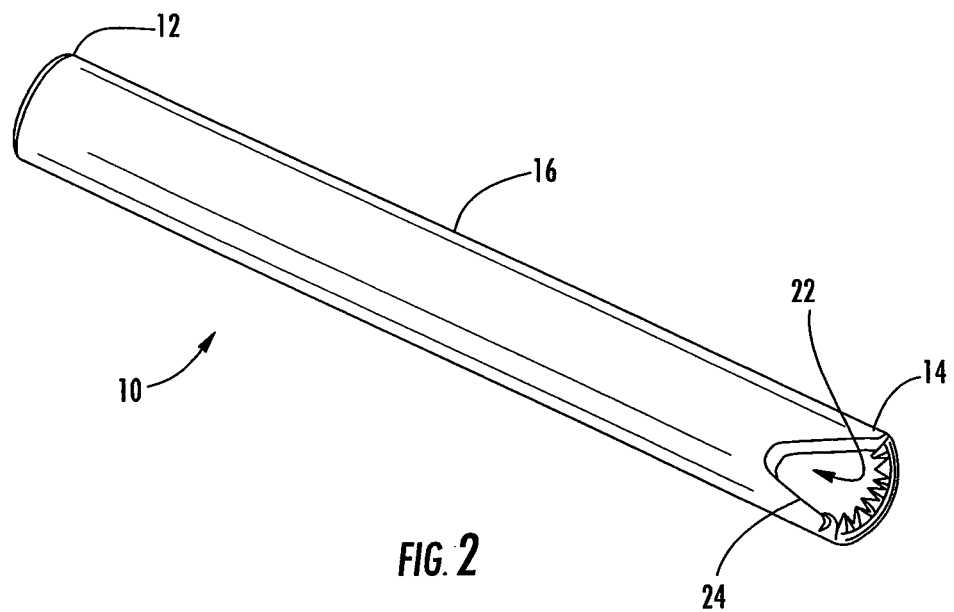
FIG. 2 is a perspective view of the opposing side of the dilator tube illustrated in FIG. 1.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The present invention is directed towards instruments for use in methods for the fixation and/or stabilization of vertebral bodies. Referring to FIGS. 1-4, an illustrative embodiment of a dilator tube, referred to generally as dilator tube 10, is shown. The dilator tube 10 contains a first proximal end 12 (i.e. the end that is closest to the surgeon and sticks out of the patient when the dilator tube 10 is inserted into a patient), a second distal end 14 (i.e. the end that contacts the vertebral body when in use) and a main body 16 there between. The main body is defined by a continuous wall 18 which provides for the generally cylindrical overall shape. Positioned at the first proximal end 12 is an opening 20 which exposes a hollow interior lumen 22 which spans the length of the main body 16, from the proximal end 12 to the distal end 14. The opening 20 and the interior lumen 22 are sized to receive and hold other spinal surgical instruments which can be inserted therein.

Figure 3:
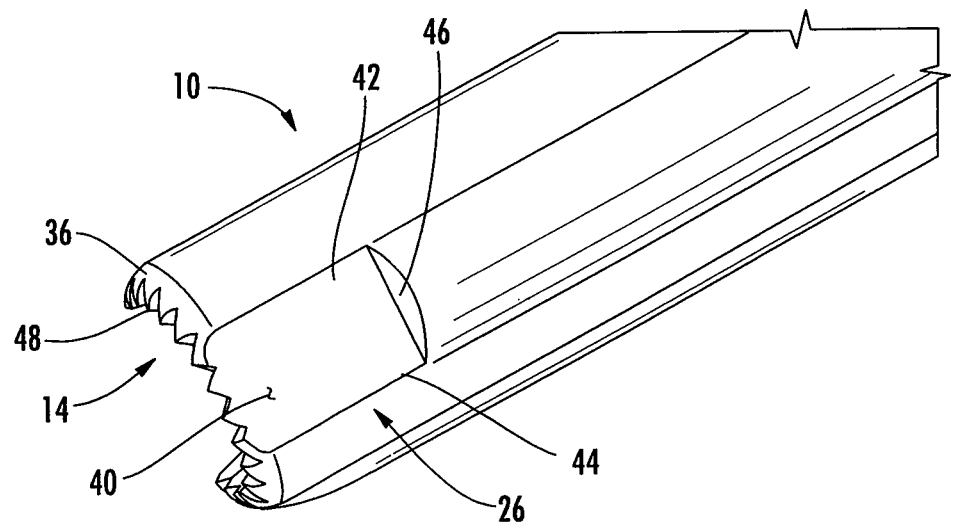
FIG. 3 is a perspective view of the dilator tube illustrated in FIG. 1, illustrating a close-up view of the distal end.
Figure 4:
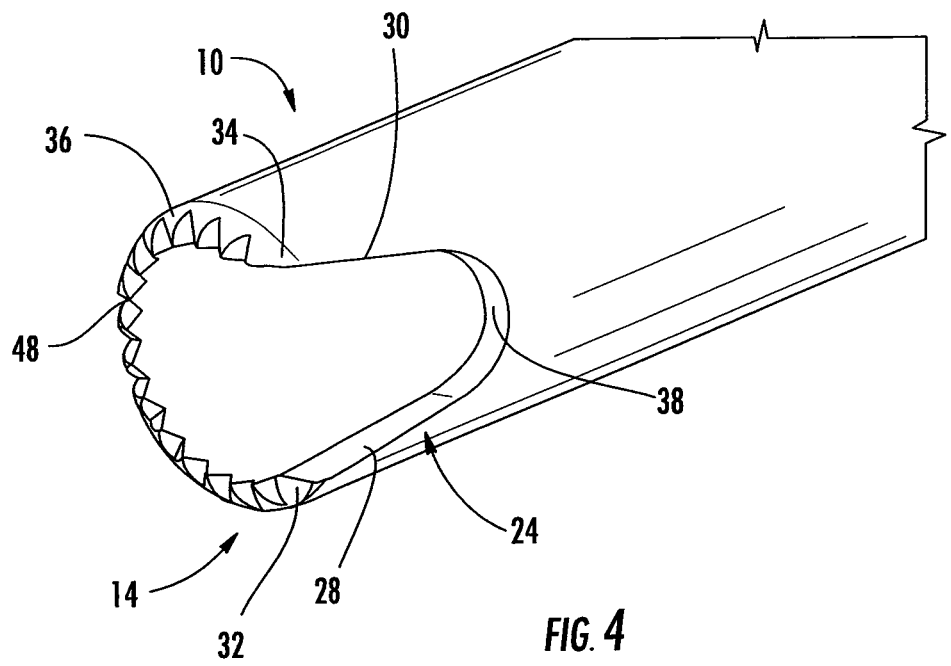
FIG. 4 is a perspective view of the dilator tube illustrated in FIG. 1, illustrating a close-up view of the opposing side of the distal end.

Referring to FIGS. 3 and 4, close-up views of the distal end 14 are shown. The distal end includes a plurality of locating or positioning members, a transverse process side window 24 and a facet flat edge 26. The transverse process side window 24 is preferably aligned in a diametrically opposed position relative to the facet flat edge 26 thereby allowing for the surgeon to properly align the dilator 10 in its proper orientation. The transverse process side window 24 is formed by walls 28 and 30 which extend from opposing ends 32 and 34 of a partial diametric surface 36 inward into the interior lumen 22. The walls 28 and 30 are preferably partially angled inwardly, but may include portions that form a generally parallel relationship. A curved or concave surface 38 connects walls 28 and 30.

The facet flat edge 26 is positioned along the wall 18 and formed as a recessed area therein. The facet flat edge 26 contains a flat, planar surface 40 extending from the partial diametric surface 36 inwardly towards the proximal end 12. The flat, planar surface 40 is cut into the continuous wall 18 and is bounded by side walls 42 and 44 and by end wall 46. The partial diametric surface 36 preferably contains one or more vertebra engagement members, illustrated herein as a plurality of angled teeth 48. Alternatively, the vertebra engagement members may include, for example, one or more spikes, or sharp bodies for engaging a patient's vertebra. As illustrated, portions of the flat surface 40 contain or form part of the plurality of angled teeth 48.

Figure 5:
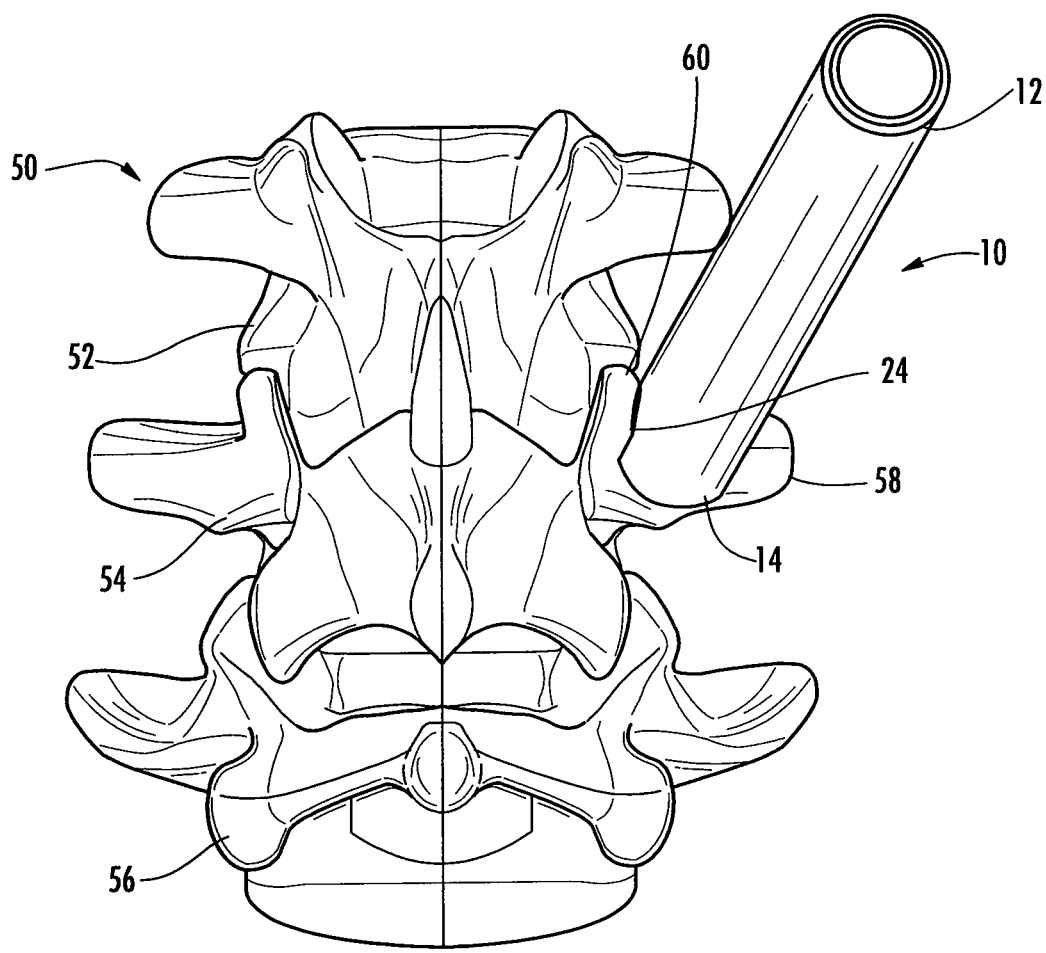
FIG. 5 is a posterior view of a plurality of spinal vertebrae with a dilator tube in accordance with the present invention attached thereto.
Figure 6:
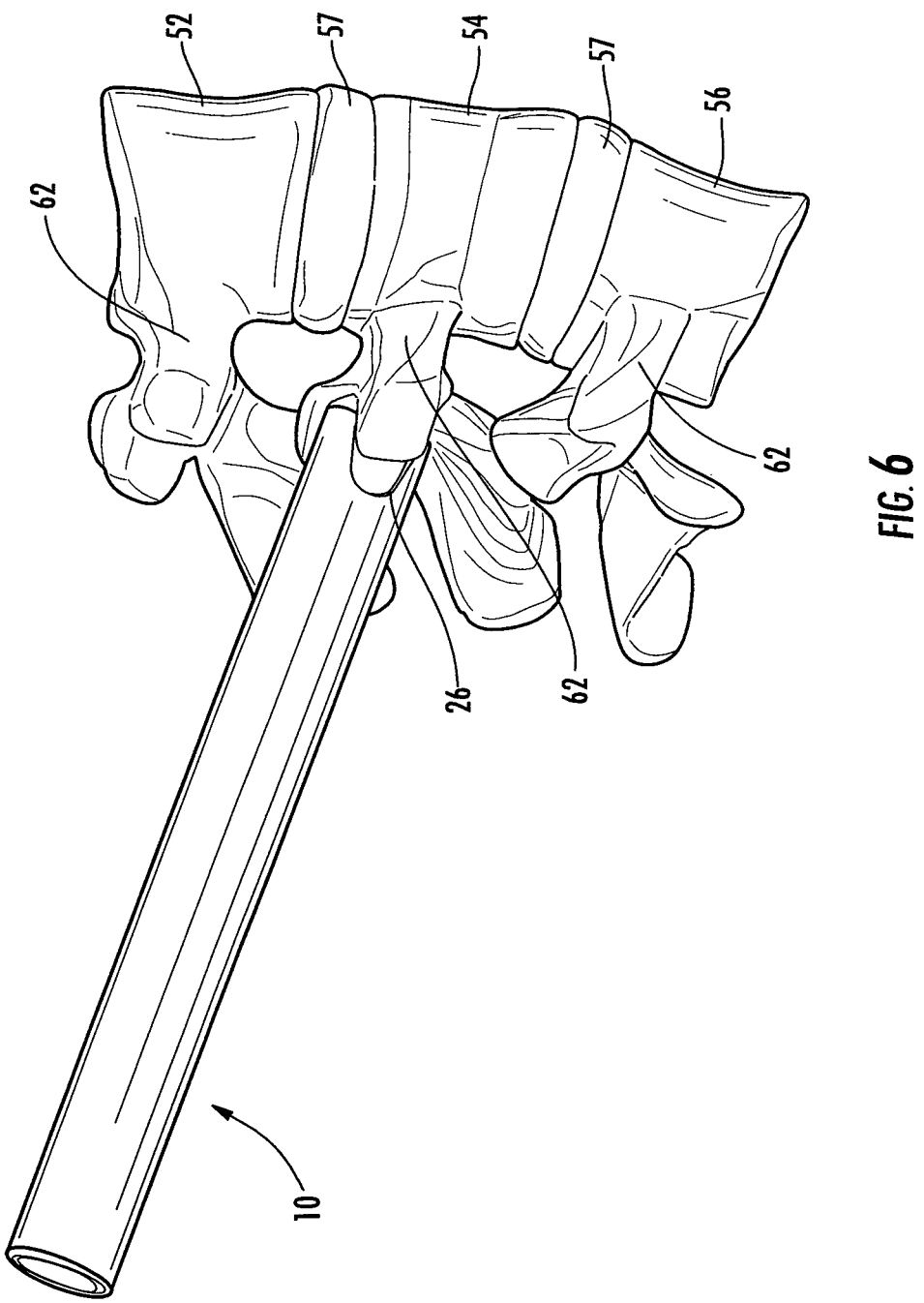
FIG. 6 is a side view of a plurality of spinal vertebrae with the dilator tube in accordance with the present invention attached thereto.
Figure 7:
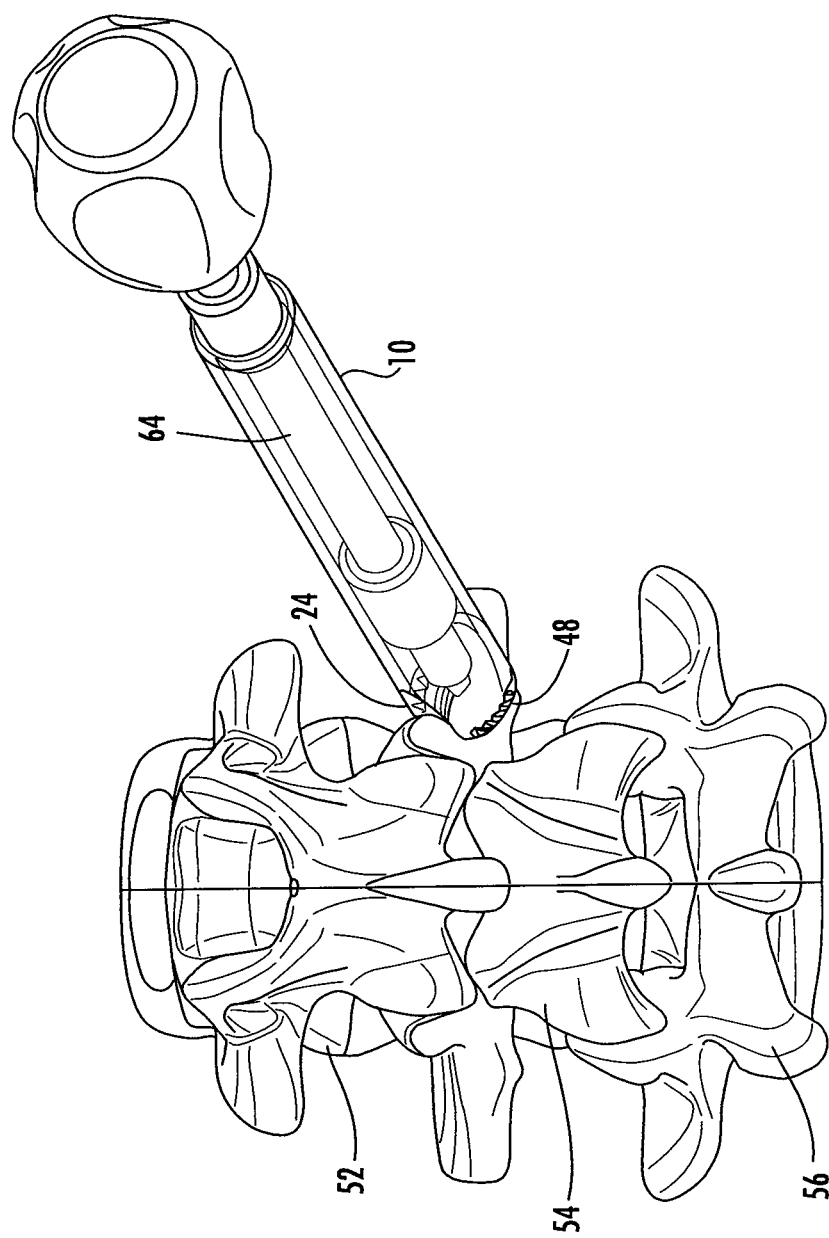
FIG. 7 is a posterior view of a plurality of spinal vertebrae with the dilator tube in accordance with the present invention attached thereto and containing match fit instrumentation, illustrated as a bone awl, inserted therein.
Figure 8:
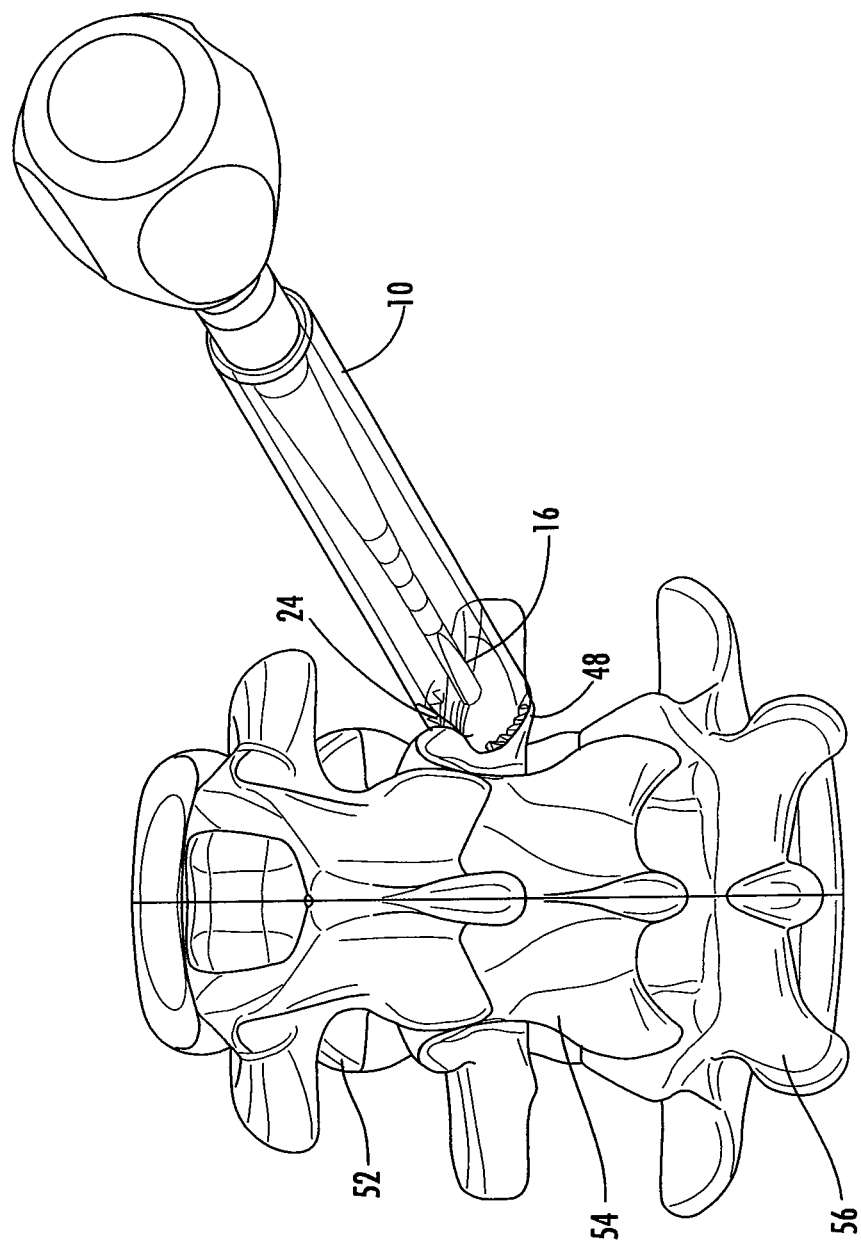
FIG. 8 is a posterior view of a plurality of spinal vertebrae with the dilator tube in accordance with the present invention attached thereto and containing match fit instrumentation, illustrated as a pedicle probe, inserted therein.
Figure 9:
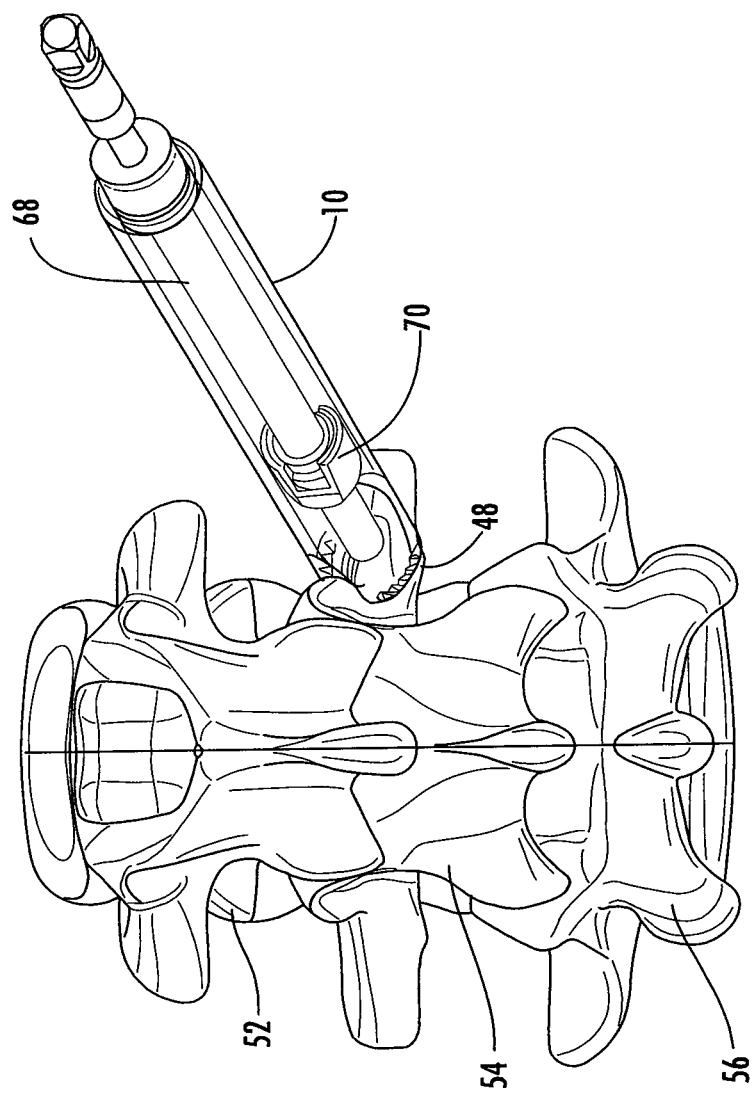
FIG. 9 is a posterior view of a plurality of spinal vertebrae with the dilator tube in accordance with the present invention attached thereto and containing match fit instrumentation, illustrated as a pedicle screw driver, inserted therein.

The present system and devices can be used by a surgeon when performing a medical procedure such as a spinal fusion which requires the insertion of pedicle screws and rods. Preferably, techniques using minimally invasive surgical techniques known to one of skill in the art are utilized. As an illustrative example, a posterior approach is utilized by the surgeon, creating a small incision in the middle of the back over the area of the spine that is to be fused. FIGS. 5 and 6 illustrate the dilator tube 10 secured to a portion of a spine made of vertebrae 52, 54, and 56, each separated by an intervertebral disc 57. The distal end 14 of the dilator tube 10 is inserted into the vertebra 54, positioned between the spinous process 58 and a portion of the spine that makes up a superior facet joint 60. The proximal end 12 extends out of the patient. The dilator tube 10 is inserted into position so that the transverse process side window 24 and a facet flat edge 26 align with the spinous process 58 and the portion of the spine that makes up a superior facet joint 60 respectively, thereby insuring proper alignment with the pedicle 62. Once in the proper position, the dilator tube 10 can be used by the surgeon to pass a series of diametrically matched pedicle insertion instruments, including a bone awl 64 to help penetrate portions of the bone (see FIG. 7), a pedicle probe 66 to aid in position verification (FIG. 8), and a pedicle screw driver 68 to aid in the insertion of a pedicle screw 70 (FIG. 9).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical device for use in surgical procedures for fixation or stabilization of vertebral bodies comprising:
    an elongated body having a first proximal end, a second distal end configured for engaging multiple portions of a spinal vertebrae when in use, and an intermediate portion defined by a continuous wall extending between said proximal end and said distal end;
    said second distal end having a circumferential end having a partial diametric surface, a first alignment member having a planar recessed surface formed within said continuous wall, and a second alignment member aligned in a diametrically opposed position relative to said first alignment member, said second alignment member containing a cut out portion positioned within one side of said continuous wall and extending to said circumferential surface, said cut out portion defining a space which separates a portion of said continuous wall and a gap between portions of said circumferential end thereby forming said partial diametric surface, each of said first alignment member and said second alignment member configured for positioning said elongated body within a portion of a vertebral body, said first alignment member planar recessed surface sized and shaped to engage with at least a portion of a spine that makes up a superior facet joint and said second alignment member sized and shaped to engage with at least a portion of a spinous process, said circumferential end contains one or more vertebra engagement member teeth.

2. The surgical device for use in surgical procedures for fixation or stabilization of vertebral bodies according to claim 1 wherein said first alignment member planar recessed surface is bounded by a pair of side walls and an end wall.

3. The surgical device for use in surgical procedures for fixation or stabilization of vertebral bodies according to claim 1 wherein said second alignment member includes a pair of inwardly directed walls separated by said space.

4. The surgical device for use in surgical procedures for fixation or stabilization of vertebral bodies according to claim 3 wherein said pair of inwardly directed walls are connected by a curved surface.

5. The surgical device for use in surgical procedures for fixation or stabilization of vertebral bodies according to claim 3 wherein said pair of inwardly directed walls are angled inwardly.

6. The surgical device for use in surgical procedures for fixation and/or stabilization of vertebral bodies according to claim 1 wherein said first proximal end comprises an opening, said opening exposing a hollow interior lumen which spans the length of the said elongated body from said proximal end to said distal end.

7. The surgical device for use in surgical procedures for fixation and/or stabilization of vertebral bodies according to claim 6 wherein said opening and said interior lumen are sized and shaped to receive and hold surgical instruments inserted therein.

8. A surgical device for use in surgical procedures for fixation or stabilization of vertebral bodies comprising:
    an elongated body having a first proximal end having an opening, said first proximal end opening exposing an interior lumen which spans the length of the said elongated body, a second distal end having a partial circular surface and configured for engaging multiple portions of a spinal vertebrae when in use, and an intermediate portion extending between said proximal end and said distal end, said intermediate portion defined by a continuous wall forming a generally tubular shape;
    said second distal end having a partial circular edge, a first alignment member having a planar recessed surface formed within said continuous wall and configured to engage with a portion of a spine that makes up a superior facet joint, and a second alignment member aligned in a diametrically opposed position relative to said first alignment member, said second alignment member configured for engaging a portion of a spine that makes up a spinous process of a vertebral body and comprising a cut out portion positioned within one side of said continuous wall and extending to a circumferential surface, said cut out portion defining a space which separates a portion of said continuous wall and a gap between portions of said circumferential surface, said cut out portion in communication with said interior lumen.

* * * * *